United States Patent [19]

Quay et al.

[11] Patent Number: 4,859,451
[45] Date of Patent: * Aug. 22, 1989

[54] PARAMAGNETIC CONTRAST AGENTS FOR MR IMAGING

[75] Inventors: Steven C. Quay; Dilip M. Worah, both of Menlo Park, Calif.

[73] Assignee: Salutar, Inc., Sunnyvale, Calif.

[*] Notice: The portion of the term of this patent subsequent to Aug. 18, 2004 has been disclaimed.

[21] Appl. No.: 855,223

[22] Filed: Apr. 24, 1986

Related U.S. Application Data

[63] Continuation-in-part of Ser. No. 657,676, Oct. 4, 1984, Pat. No. 4,687,658, and a continuation-in-part of Ser. No. 671,106, Nov. 11, 1984, Pat. No. 4,687,659.

[51] Int. Cl.$^4$ ............... A61K 49/00; G01N 31/00
[52] U.S. Cl. ..................... 424/9; 128/653; 128/654; 536/173; 536/806; 556/45; 556/51; 556/57; 556/83; 556/110; 556/118; 556/136; 556/138
[58] Field of Search .............. 424/9; 436/173, 806; 128/653, 654; 556/148, 45, 51, 57, 83, 110, 118, 136, 138

[56] References Cited

U.S. PATENT DOCUMENTS 3,859,337 2/1975 Herz et al.
4,647,447 3/1987 Gries et al. ..................... 424/4
4,687,658 8/1987 Quay ..................... 424/9
4,687,659 8/1987 Quay ..................... 424/9

FOREIGN PATENT DOCUMENTS

86330/82   1/1983  Australia .
0130934 A1 1/1985  European Pat. Off. .
0133603 A1 2/1985  European Pat. Off. .
3324236 A1 1/1985  Fed. Rep. of Germany .
2137612   10/1984  United Kingdom ......... 556/148
2137612 A 10/1984  United Kingdom .

OTHER PUBLICATIONS

Chemical Abstracts, 81:77423v (1974).
Chemical Abstracts, 90:203450c (1979).
Chemical Abstracts, 101:216407q (1984).
Pykett Ian L., Scientific American, pp. 78–88 (May, 1982).

Primary Examiner—Robert J. Warden
Assistant Examiner—Stephen C. Wieder
Attorney, Agent, or Firm—William B. Walker

[57] ABSTRACT

In the NMR imaging of a subject comprising administering to such subject a composition containing an image-modifying effective amount of an image enhancer, permitting the enhancer to move through the subject, and after a time interval taking an NMR image of the subject, the improvement which comprises employing as said enhancer a complex of a paramagnetic polyvalent metal and a partial amide and/or ester of diethylenetriaminepentaacetic acid. The complexes are new.

17 Claims, No Drawings

PARAMAGNETIC CONTRAST AGENTS FOR MR IMAGING

CROSS-REFERENCE TO RELATED APPLICATION

This is a continuation-in-part of patent application Ser. Nos. 657,676, filed Oct. 4, 1984, now U.S. Pat. No. 4,687,658 and Ser. No. 671,106, filed Nov. 11, 1984, now U.S. Pat. No. 4,687,659.

BACKGROUND OF THE INVENTION

The present invention relates to improvements in the enhancing of nuclear magnetic resonance (NMR) imaging of a subject, e.g., organs of a patient.

X-rays have long been used to produce images of internal organs of a patient, the patient being positioned between a source of X-rays and a film sensitive to the rays. Where organs interfere with the passage, the film is less exposed and the resulting picture, upon development of the film, is an indication of the state of the organ.

More recently, another imaging technique has been developed, viz. nuclear magnetic resonance. This avoids the harmful effects sometimes attending X-ray exposure. For improved imaging, with X-rays patients have been given enhancers prior to imaging, either orally or parenterally. After a predetermined time interval for distribution of the enhancer through the patient, the image has been taken. The time of good imaging is desirably as short as possible after taking the enhancer; on the other hand there is a decay in effectiveness, so desirably the decay is relatively slow so as to provide a substantial time interval during which imaging can be done. The present invention relates to enhancers in NMR imaging.

Australian application No. 86-330/82 of July 22, 1982 discloses use as an NMR image enhancer of a complex salt, preferably the gadolinium chelate of diethylenetriaminepentaacetic acid, plus an amine. From the data reported therein these appear to perform well. However, this compound is highly ionic and is rapidly excreted by the kidneys, making the timing of the injection extremely critical. Furthermore, there is virtually no uptake by any solid organ, such as the heart, pancreas or liver. Moreover, an amine is also required.

SUMMARY OF THE INVENTION

It is accordingly an object of the present invention to provide alternative image enhancers which avoid one or more of the aforementioned disadvantages.

It is another object of the invention to reduce the total number of particles from three to one, thereby decreasing the osmolarity and improving the safety, without affecting the efficacy of the compound.

It is still another object of the present invention to attain a 3- to 4- fold improvement in efficacy.

It is a further objective of the invention to obtain a compound which will work in the heart or liver.

These and other objects and advantages are realized in accordance with the present invention pursuant to which the image enhancer comprises a complex of a paramagnetic metal and a partial amide and/or ester of diethylenetriaminepentaacetic acid.

DETAILED DESCRIPTION OF THE INVENTION

While lanthanides and particularly gadolinium are highly paramagnetic and useful in accordance with the invention, it is surprising that other less paramagnetic metals perform well, e.g., iron, manganese, copper, cobalt, chromium and nickel.

The complexing or chelating agent has the structural formula

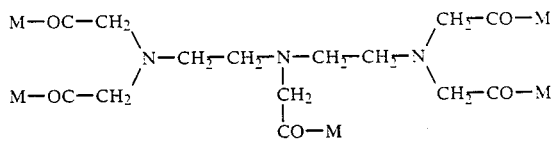

in which
from 1 to 4, advantageously 2 or 3, and preferably 2 M's are OH, the balance independently are OR, $NH_2$, NHR and/or NRR, and
R is an organic alkyl radical, preferably an optionally substituted alkyl radical of 1 to 18 carbon atoms, of the general formula $-(CH_2)_n CH_3$.

The chelating agent can be produced by amidating and/or esterifying the pentaacetic acid, which is commercially available, in conventional manner with an amine and/or an alcohol, simultaneously or sequentially when a product is desired wherein all the M's other than those which are hydrogen are not identical. Thus, the pentaacetic acid may be reacted with two moles of ammonia or a primary or secondary amine to produce a diamide, or with two moles of an alcohol to produce a diester. Alternatively, the pentaacetic acid can be reacted with one mole of ammonia or amine to produce a mono-amide and then with one mole of alcohol to produce a mono-amide-mono-ester triacetic acid.

Alternatively, the starting material instead of the pentaacetic acid can be the dianhydride thereof, also commercially available, and this can be amidated and/or esterified as follows, for example;

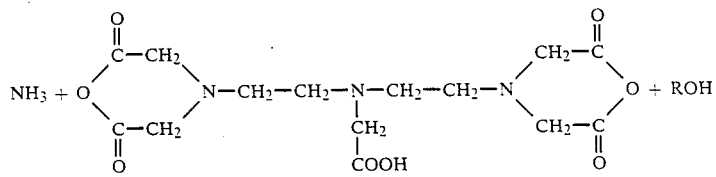

-continued

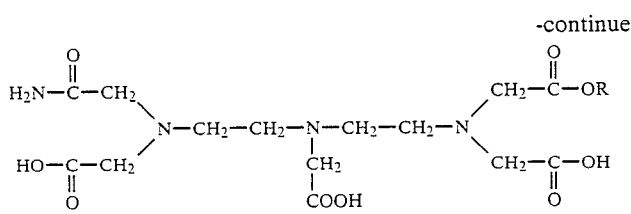

The complex can be prepared by dissolving the amide/ester in water or other solvent and adding a salt of the desired metal, e.g., ferric chloride. The solution can then be dialyzed or ion exchanged to remove chloride ions or an alkali such as NaOH can be added to neutralize the chloride ions, the by-product NaCl being removed or left in solution since it is physiologically acceptable.

Where the complexing metal is of a higher valence state than the complexing agent can accept, e.g., $M(+4)$ with a complexing agent having three binding sites, the fourth M valence may be tied up as the chloride. When the metal is only divalent, for example $Cu(+2)$, the extra site of the complexing agent may be neutralized as the sodium salt.

When the amide is substituted, or with an ester, as the chain length increases, the complexes become increasingly oleophilic and chains of 12 or more carbon atoms slow down the movement to the kidneys due to temporary entrapment or enrichment in organs which have efficient fatty acid uptake systems such as the hepatobiliary system. Thus, such acylates are especially useful for liver imaging. Other organs such as the kidney, ureter, bladder, brain and heart can be imaged well with the lower homologues or non-acylated complexes. Since the complexes do not penetrate the blood-brain-barrier under normal circumstances, they are useful in detecting the extravasation of arterial blood in the extravascular space during cerebral hemorrhaging and in the edema fluid surrounding tumors.

As noted, iron (III) is the preferred metal ion, but other polyvalent paramagnetic metals ions may be used, e.g., manganese, chromium, cobalt, nickel, copper, and the like. The preferred lanthanide is gadolinium, but others such as lanthanum, cerium, praseodymium, neodymium, promethium, samarium, europium, terbium, dysprosium, holmium, erbium, thulium, ytterbium and lutetium may also be used.

The images can be taken in conventional manner using any of the machines currently available, e.g., that of Siemens AG of Erlanger, Federal Republic of Germany.

Further details of imaging systems are described in the prior art, e.g., "NMR A Primer for Medical Imaging" by Wolf and Popp Slack Book Division (ISBN 0-943432-19-7) and *Scientific American*, May 1982, pages 78–88.

The solution of complex may be sterilized and made up into ampules or may be lyophilized into a pwder for dissolution when ready to be used. The solution may be mixed with conventional additives such as saline solution, albumin, buffers and the like. If desired, ampules may be made up containing lyophilized powder of the complex in one compartment and a solution of additives in another separated from the first by a frangible barrier. When ready to use, the barrier is broken and the ampule shaken to form a solution suitable for use.

Immediately prior to actual administration of the contrast agent, the reconstituted solution is further diluted by addition of at least 100 ml (up to 1000 ml) of a suitable diluent such as;
Roger's Injection, USP
Sodium Chloride Injection, USP
Dextrose Injection, USP
  (5 percent Dextrose in sterile water)
Dextrose Sodium Chloride Injection, USP
  (5 percent Dextrose in Sodium Chloride)
Located Ringer's Injection, USP
Protein Hydrolysate Injection
  Low Sodium, USP 5 percent
  5 percent with Dextrose 5 percent
  5 percent with Invert Sugar 10 percent
Roger's Injection, USP
Roger's Injection, USP The manner and dosage of administration and the manner of scanning are substantially the same as in the prior art. With solutions containing about 50 to 200 mmoles of the complex liter, sufficient solution should be administered orally or parenterally to provide about 1 100 $\mu$mols/kg, corresponding to about 1 to 50 mmol for an adult human patient. For smaller patients or other animals, the dosage should be varied accordingly. The particular complex and organ to be imaged will determine the waiting period between administration and imaging. For kidney imaging the cortical-medulla enhancement phase occurs 15–45 seconds after injection. For the heart and liver, the uptake occurs between 2 and 10 minutes after injection.

The invention will be further described in the following illustrative examples wherein all parts are by weight unless otherwise expressed.

EXAMPLES

EXAMPLE 1: Synthesis of Alkylamine DTPA Derivatives (1) 5 g (14 mmol) of diethylenetriaminepentaacetic acid anhydride (Sigma Chemical Company) is placed in a round bottomed flask and 60 ml of chloroform are added. The mixture is stirred vigorously with a magnetic stirrer till all clumps of the anhydride are dispersed.

(2) A 4-fold molar excess of hexyl amine (Aldrich Chemical Co.) (56 mmol) is gradually added to the stirring mixture.

(3) The reaction is allowed to continue for an additional hour with constant stirring. At this point, the reaction mixture is light yellow and clear.

(4) The chloroform and excess hexyl amine is removed with a rotary evaporator and the resulting solids are washed twice in 95% ethanol and dried in a vacuum at room temperature overnight.

The formula weight of the compound is 560.71. and its structure is

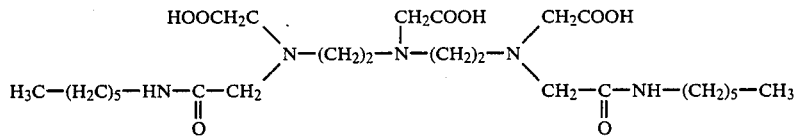

A gadolinium chelate of the compound was made in the following way:

(1) 28.04 (0.05 mol) of the compound was dissolved in 400 ml water.

(2) The pH of the dissolved material was adjusted to 4 and 18.59 g (0.05 mol) of gadolinium chloride hexahydrate (99.999%, (Alderich Chemical Co.) was added to the stirring mixture.

(3) The resulting drop in pH was gradually adjusted to 6.5 with a 5N solution of sodium hydroxide.

(4) The volume of the solution was brought to 500 ml with distilled water. The clear, pale yellow solution was filtered through a 0.2μ filter and stored in 30 ml vials sealed with a butyl rubber stopper.

Relaxivity of the compound in water and in human plasma at 10 MHz (37° C.) (for practical purposes, the lower the $T_1$ in a given part of the body, the brighter the image in MR imaging):

| Gd DTPA dihexyl amide (inventive compound) (millisec) | | | | |
|---|---|---|---|---|
| Conc M | *$T_1$ Plasma | *$T_2$ Plasma | *$T_1$ Water | *$T_2$ Water |
| $9.34 \times 10^{-3}$ | 15 | 10 | 23 | 18 |
| $4.67 \times 10^{-3}$ | 26 | 21 | 42 | 36 |
| $2.34 \times 10^{-3}$ | 48 | 39 | 81 | 76 |
| $1.17 \times 10^{-3}$ | 83 | 73 | 159 | 147 |
| $5.84 \times 10^{-4}$ | 145 | 123 | 309 | |
| $2.92 \times 10^{-4}$ | 249 | | 561 | |
| $1.46 \times 10^{-4}$ | 403 | | 947 | |
| $7.30 \times 10^{-5}$ | 622 | | 1374 | |
| $3.65 \times 10^{-5}$ | 881 | | | |
| $1.82 \times 10^{-5}$ | 1087 | | | |
| $9.12 \times 10^{-6}$ | 1220 | | | |

| Gd DTPA Di-N—methylglucamide (N—MG) (prior art compound) | | | | |
|---|---|---|---|---|
| Conc M | *$T_1$ Plasma | *$T_2$ Plasma | *$T_1$ Water | *$T_2$ Water |
| $6.25 \times 10^{-3}$ | 39 | 31 | 40 | 35 |
| $3.13 \times 10^{-3}$ | 69 | 61 | 83 | 76 |
| $1.56 \times 10^{-3}$ | 134 | 116 | 163 | 155 |
| $7.81 \times 10^{-4}$ | 240 | | 309 | |
| $3.91 \times 10^{-4}$ | 405 | | 582 | |
| $1.95 \times 10^{-4}$ | 636 | | 1015 | |
| $9.77 \times 10^{-5}$ | 877 | | | |

*$T_1$ and $T_2$ are relaxation times.

It is surprising that the Gd DTPA dihexyl amide is almost three times better at proton relaxation in plasma than the prior art of Gd DTPA (N-MG).

Without wishing to be bound by any particular theory of operability, this enhanced relaxivity is probably due to protein binding in plasma by the oleiphilic derivatives. Koenig and Brown (S. H. Koenig and R. D. Brown, *Magnetic Resource in Medicine* 1, 478–495, (1984)) teaches that changes in rotational correlation times, which should accompany the protein binding of small paramagnetic molecules, can give a substantial improvement in proton relaxivity. This can potentially allow lower doses in humans and thus provide a safer product.

EXAMPLE 2: Pharmacokinetics of the compound in a pure breed beagle dog

A male dog was injected with the compound at 100μ mol/kg. Blood was drawn at the indicated times. The plasma was separated and the relaxivity measured.

| Time min. | $T_1$ Gd DTPA hexyl amide (inventive compound) | $T_1$ Gd DTPA (prior art compound) |
|---|---|---|
| Pre-inj | 1517 | 1427 |
| 10 | | 440 |
| 20 | 275 | 444 |
| 30 | 362 | 551 |
| 45 | 447 | 580 |
| 60 | 688 | 687 |
| 90 | 965 | 860 |
| 180 | 1340 | 1282 |
| 360 | 1610 | |

Again, applicants were surprised that, at the same dosage the inventive compound produced a blood $T_1$ value (275 msec) at 20 minutes which was substantially lower than the prior art compound (444 msec). This will produce a two-fold improvement in image signal intensity.

EXAMPLE 3: Organ distribution of the compound in male rabbits

The compound was injected into male rabbits at 100μ mol/kg. The rabbits were sacrificed at 15 minutes post injection and the relaxivity of internal organs was measured in vitro at 5 MHz.

| Organ | $T_1$ (msec) Gd DTPA hexyl amide (inventive compound) | Gd DTPA (prior art compound) | $T_1$ (msec) normal organs |
|---|---|---|---|
| Heart | 374 | 487 | 482 |
| Lung | 507 | 565 | 585 |
| Fat | 167 | 173 | 180 |
| Skeletal Muscle | 397 | 405 | 411 |
| Renal Cortex | 179 | 242 | 342 |
| Renal Medulla | 218 | 379 | 782 |
| Liver | 176 | 251 | 260 |
| Spleen | 362 | 463 | 473 |
| Pancreas | 256 | 253 | 265 |
| Bladder | 308 | 272 | 511 |
| Stomach | 332 | 312 | 305 |
| Small Intestine | 248 | 298 | 317 |
| Large Intestine | 183 | 317 | 328 |

It is noted that the prior art compound fails to produce any change in spin-lattice ($T_1$) relaxation in the heart and liver and thus would produce no noticeable image enhancement in these organs. Applicants' invention is very effective in lowering $T_1$ in the liver and heart and thus produces image signal enhancement in these organs.

It will be understood that the specification and examples are illustrative but not limitative of the present invention and that other embodiments within the spirit and scope of the invention will suggest themselves to those skilled in the art.

What is claimed is:

1. A complex of a paramagnetic polyvalent metal and a derivative of diethylenetriaminepentaacetic acid of the formula $$\begin{array}{c} \text{M—OC—CH}_2 \\ \phantom{\text{M—OC—CH}_2}\diagdown \\ \phantom{\text{M—OC—CH}_2}\phantom{\diagdown}\text{N—CH}_2\text{—CH}_2\text{—N—CH}_2\text{—CH}_2\text{—N} \\ \phantom{\text{M—OC—CH}_2}\diagup \phantom{\text{N—CH}_2\text{—CH}_2\text{—}}| \\ \text{M—OC—CH}_2 \phantom{\diagup\text{N—CH}_2} \text{CH}_2 \\ \phantom{\text{M—OC—CH}_2\diagup\text{N—CH}_2\text{—}}| \\ \phantom{\text{M—OC—CH}_2\diagup\text{N—CH}_2} \text{CO—M} \end{array} \quad \begin{array}{c} \text{CH}_2\text{—CO—M} \\ \diagup \\ \\ \diagdown \\ \text{CH}_2\text{—CO—M} \end{array}$$

in which
from 1 to 4 M's are OH and the balance independently are OR, NH$_2$, NHR or NRR, and
R is an alkyl radical of 1 to 18 carbon atoms.

2. A complex according to claim 1, wherein the metal is selected from the group consisting of a lanthanide, iron, manganese, copper, cobalt, chromium and nickel.

3. A complex according to claim 1, wherein the metal is selected from the group consisting of iron, manganese and gadolinium.

4. A complex according to claim 1, wherein two of the acid radicals of the diethylenetriaminepentaacetic acid are amide or ester substituted.

5. A complex according to claim 1 wherein an amide group is present and its nitrogen is substituted by at least one C$_{1-18}$-alkyl radical.

6. A complex according to claim 1, wherein the amide or ester radical includes at least one chain of at least 4 carbon atoms.

7. A complex according to claim 1, wherein the amide or ester radical includes at least one chain of at least 12 carbon atoms.

8. A complex according to claim 1, wherein the metal is iron.

9. A complex according to claim 6, wherein the metal is selected from the group consisting of iron, manganese and gadolinium.

10. In the NMR imaging of a subject comprising administering to such subject a composition containing an image-modifying effective amount of an image enhancer, permitting the enhancer to move through the subject, and after a time interval taking an NMR image of the subject, the improvement which comprises administering as said enhancer a complex according to claim 1.

11. A process according to claim 10, wherein the metal of the complex is selected from the group consisting of a lanthanide, iron, manganese, copper, cobalt, chromium and nickel.

12. A process according to claim 10, wherein the metal of the complex is selected from the group consisting of a iron, manganese, and gadolinium.

13. A process according to claim 10, wherein two of the acid radicals of the diethylenetriaminepentaacetic acid are amide or ester substituted.

14. A process according to claim 10, wherein an amide group is present and its nitrogen is substituted by at least one C$_{1-18}$-alkyl radical.

15. A process according to claim 10, wherein the amide or ester radical includes at least one chain of at least 4 carbon atoms.

16. A process according to claim 10, wherein the amide or ester radical includes at least one chain of at least 12 carbon atoms.

17. A process according to claim 13, wherein the metal is iron.

* * * * *